United States Patent
Bruder et al.

(10) Patent No.: US 11,160,537 B2
(45) Date of Patent: Nov. 2, 2021

(54) APPARATUS AND METHOD FOR REAL-TIME TRACKING OF TISSUE STRUCTURES

(71) Applicant: Varian Medical Systems, Inc., Palo Alto, CA (US)

(72) Inventors: Ralf Bruder, Luebeck (DE); Achim Schweikard, Hamburg (DE)

(73) Assignee: Varian Medical Systems, Inc., Palo Alto, CA (US)

( * ) Notice: Subject to any disclaimer, the term of this patent is extended or adjusted under 35 U.S.C. 154(b) by 1481 days.

(21) Appl. No.: 14/854,274

(22) Filed: Sep. 15, 2015

(65) Prior Publication Data

US 2016/0000409 A1   Jan. 7, 2016

Related U.S. Application Data

(63) Continuation of application No. PCT/US2014/027367, filed on Mar. 14, 2014.

(60) Provisional application No. 61/799,889, filed on Mar. 15, 2013.

(51) Int. Cl.
*A61B 8/08* (2006.01)
*A61B 6/00* (2006.01)
*A61B 6/03* (2006.01)
*A61B 8/00* (2006.01)
(Continued)

(52) U.S. Cl.
CPC ............ *A61B 8/5269* (2013.01); *A61B 6/032* (2013.01); *A61B 6/4417* (2013.01); *A61B 8/085* (2013.01); *A61B 8/0833* (2013.01); *A61B 8/0883* (2013.01); *A61B 8/4245* (2013.01); *A61B 8/4416* (2013.01); *A61B 8/4483* (2013.01); *A61B 8/466* (2013.01); *A61B 8/5261* (2013.01); *A61B 8/543* (2013.01); *A61N 5/1049* (2013.01); *A61B 6/4014* (2013.01); *A61B 6/4441* (2013.01);
(Continued)

(58) Field of Classification Search
None
See application file for complete search history.

(56) References Cited

U.S. PATENT DOCUMENTS

| 5,806,521 A | 9/1998 | Morimoto et al. |
| 2004/0006272 A1 | 1/2004 | Vortman et al. |
| 2004/0122323 A1 | 6/2004 | Vortman et al. |

(Continued)

FOREIGN PATENT DOCUMENTS

WO   2014/152463 A1   9/2014

OTHER PUBLICATIONS

International Search Report of PCT Application No. PCT/US2014/027367, dated Aug. 1, 2014, 4 pages.

*Primary Examiner* — Christopher Koharski
*Assistant Examiner* — Michael S Kellogg
(74) *Attorney, Agent, or Firm* — Duane Morris LLP; Manita Rawat

(57) ABSTRACT

A method and system are disclosed for radiosurgical treatment of moving tissues of the heart, including acquiring at least one volume of the tissue and acquiring at least one ultrasound data set, image or volume of the tissue using an ultrasound transducer disposed at a position. A similarity measure is computed between the ultrasound image or volume and the acquired volume or a simulated ultrasound data set, image or volume. A robot is configured in response to the similarity measure and the position of the transducer, and a radiation beam is fired from the configured robot.

14 Claims, 10 Drawing Sheets

(51) Int. Cl.
  *A61N 5/10* (2006.01)
  *A61B 90/00* (2016.01)
(52) U.S. Cl.
  CPC ..... *A61B 2090/3925* (2016.02); *A61N 5/1067* (2013.01); *A61N 2005/1058* (2013.01)

(56) References Cited

U.S. PATENT DOCUMENTS

| | | | |
|---|---|---|---|
| 2007/0015991 A1* | 1/2007 | Fu | A61B 8/08 600/407 |
| 2011/0258843 A1 | 10/2011 | Dukesherer et al. | |
| 2012/0014581 A1 | 1/2012 | Boyden et al. | |

* cited by examiner

| Tissue | Hounsfield units (min/max) | Acoustic Impedance (kg m2/s) | Acoustic Speed (m/s) |
|---|---|---|---|
| Pure air | -1000 | 0,0004 | 331 |
| Lung | -800/-500 | 0,003 | 331 |
| Fat tissue | -100/0 | 0,138 | 1468 |
| Water | -10/10 | 1,53 | 1526 |
| Liver | 40/60 | 1,65 | 1559 |
| Bones | 250/1000 | 6,66 | 3600 |
| Blood | 30/70 | 1,60 | 1562 |
| Heart tissue | 20/50 | 1,67 | 1590 |

Figure 4 : Mapping of Hounsfield values to acoustic properties

APPARATUS AND METHOD FOR REAL-TIME TRACKING OF TISSUE STRUCTURES

CROSS-REFERENCES TO RELATED APPLICATIONS

This application claims priority to and is a continuation of PCT/US2014/027367, filed Mar. 14, 2014, which claims the benefit under 35 USC 119(e) of U.S. Provisional Application No. 61/799,889 filed Mar. 15, 2013. The full disclosure of which is incorporated herein by reference in its entirety for all purposes.

This application is related to U.S. patent application Ser. No. 11/971,399 filed on Jan. 9, 2008, and entitled "Depositing Radiation in Heart Muscle under Ultrasound Guidance," the full disclosure of which is incorporated herein by reference.

FIELD OF THE INVENTION

The present invention generally relates to systems and methods for tracking anatomical targets using ultrasound. Optionally, embodiments of the present invention may be used in tracking anatomical targets during a radiosurgical procedure.

BACKGROUND OF THE DISCLOSURE

Devices for medical imaging were originally invented for the purpose of diagnosis. Recently, devices for medical imaging have been used for more than just diagnosis—medical imaging may now be used to visualize the anatomical site not only before, but also during an intervention. In this way, the intervention can be guided by the imaging device. In a radiosurgical system/procedure, image distortions in guidance images should not be ignored since inaccuracies in the guidance images will lead to inaccuracies in the treatment.

Targets such as tumors in the head, spine, abdomen and lungs have been successfully treated by using radiosurgery. During radiosurgery, the target is bombarded with a series of beams of ionizing radiation (for example, a series of MeV X-ray beams) fired from various different positions and orientations by a radiation delivery system. The beams can be directed through intermediate tissue toward the target tissue so as to affect the tumor biology. The beam trajectories help limit the radiation exposure to the intermediate and other collateral tissues, using the cumulative radiation dose at the target to treat the tumor. The CyberKnife™ Radiosurgical System (Accuray Inc.) and the Trilogy™ radiosurgical system (Varian Medical Systems) are two such radiation delivery systems.

Some systems also have an ability to treat tissues that move during respiration, and this has significantly broadened the number of patients that can benefit from radiosurgery. It has also previously been proposed to make use of radiosurgical treatments for treatment of other tissues that undergo physiological movements, including the directing of radiation toward selected areas of the heart for treatment of atrial fibrillation. Modern robotic radiosurgical systems may incorporate in-treatment imaging into the treatment system so as to verify the position of the target tissue without having to rely on rigid frameworks affixing the patient to a patient support. Recently, ultrasound has been proposed as a modality for tracking an anatomical target; however, ultrasound tracking for regions in the upper chest is difficult. For interventions in the heart, both respiratory and cardiac motion must be addressed. In the case of radiosurgery, the therapeutic beam must follow the target with high accuracy.

While ultrasound tracking during radiosurgical treatments provide benefits by significantly reducing trauma for heart patients, improvements to existing systems and methods of ultrasound tracking may be helpful to expand the use of ultrasound tracking during radiosurgical therapies.

In light of the above, it would be desirable to provide improved devices, systems, and methods for tracking tissues using ultrasound and treating tissues of a patient, particularly by directing radiation from outside the patient and into target tissues of a heart. It would be particularly beneficial if these improvements were compatible with (and could be implemented by modification of) existing radiosurgical systems, preferably without significantly increasing the exposure of patients to incidental imaging radiation, without increasing the costs so much as to make these treatments unavailable to many patients, and/or without unnecessarily degrading the accuracy of the treatments and without causing collateral damage to the healthy tissue despite the movement of the target tissues during beating of the heart.

SUMMARY OF THE DISCLOSURE

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description presented later.

The present invention generally provides improved systems and methods of tracking anatomical targets using ultrasound. Optionally, embodiments of the present invention may be used in tracking anatomical targets during a radiosurgical procedure. The apparatus and method may also be used for catheter ablation procedures as well. It can equally be used for any other surgical intervention with or without robot assistance as well. For diagnostic purposes, standardized ultrasound views are defined for two goals: 1) to find an area of undisturbed line of sight to the target, and 2) to define a standardized view where a physician can easily navigate and make his diagnosis. Trying to reach this second goal, limited imaging quality of the target region is often accepted. For tracking purposes, a standardized view is not necessary.

One difficulty for the every-day use of an ultrasound tracking system is finding an optimal view from the transducer to the target offering a high quality ultrasound image. Obtaining high quality ultrasound images mainly depends on the tissue passed in the line of sight between the ultrasound transducer and target. Further criteria for good imaging and tracking results are the distance between target and transducer and the target reflectivity according to the beam direction. While blood and muscle tissue usually have good transmission characteristics, the ribs and the air inside the lung absorb or reflect nearly 100% of the emitted ultrasound beam, virtually rendering visualization of the underlying tissue impossible. Accordingly, high quality ultrasound of a patient's chest is difficult due to the presence of air and bony structures, and due to image distortions in ultrasound.

Furthermore, tracking in radiosurgery comes with a couple of limitations which considerably increase the complexity of the ultrasound view finding problem. Some of the standardized transducer positions are generally not applicable during treatment. Patients are usually lying on their back to allow a stable registration to the planning-CT. For ultrasound visualization, patients are usually rotated to the side. In this position, the heart slightly falls in the direction of gravity and presses against the lung, reducing the air between target and skin. Without rotation, these standardized ultrasound views may not even allow visualization of the target. Moreover, target visibility over time is a problem. Continuous target visualization has to be guaranteed for a full treatment session. Ultrasound images have a tendency to faint, so the camera must be moved continuously by a human operator to keep up a readable image. Additionally, breathing commands to deflate the lung, resulting in an enhanced target visibility for a short time are not applicable, as a stream of high quality images of the anatomical target are needed throughout the therapy.

In accordance with one aspect of the invention, imaging quality of an ultrasound transducer placed at a certain skin position is estimated prior to obtaining ultrasound image data. The image quality may be estimated by analyzing the route from a transducer position to a chosen target. The route information may be provided by image data from a preoperative imaging modality such as CT, x-ray, MRI, PET, etc. Based on the preoperative images of the anatomical site, ultrasound velocity may be estimated in each of the tissues disposed along the route from the position of the transducer to the target. A virtual ultrasound beam may be propagated through the tissues disposed along the route in the preoperative image data using a ray casting method. Thereafter, the ultrasound transmission between the position and target may be estimated and displayed to an operator. A plurality of image quality estimates may be calculated to determine a position with the highest estimated ultrasound quality. Additionally, ultrasound image quality may be calculated over a period of time for each position to determine how the image quality may change with respiration and/or heartbeat movement of the patient. Further, once a desired ultrasound imaging position is determined and while acquiring ultrasound image data from the position, a distortion in the acquired image data may be compensated by analyzing the route between the ultrasound transducer and the target in the pre-operative imaging data.

In accordance with another embodiment of the invention, an ultrasound camera is used to track a moving anatomical target, where the distortion of the ultrasound camera is compensated by observing a sequence of positions of the target or a surrogate of this target in another image modality. This second image modality may be configured to deliver images infrequently or less frequently than the ultrasound camera, but may be calibrated in such a way that distortions remain small or negligible. The motion curves of the target resulting from both the ultrasound sequence and the second image modality are then overlaid and a computation is performed to subtract the distortion effects in the ultrasound image sequence. Since ultrasound may deliver a stream of image data, with more than 20 images per second for example, the method according to this embodiment of the invention will yield a stream of low-distortion images. A method for analyzing the ultrasound images can then be applied to obtain target position information on the precise location of the target during a treatment. For periods of poor visibility, the in-treatment position can be inferred from the past observations through an extrapolation of the motion pattern in time, until the target will again become visible. Accordingly, respiratory motion and cardiac motion can be addressed. The above methods may be incorporated individually or in combination with radiosurgical systems and methods to provide target tracking with reduced patient exposure to radiation.

In some embodiments of the present invention, a method for providing ultrasound image guidance data is provided. The method includes imaging an anatomical site including a target with an ultrasound camera to generate a stream of ultrasound data of the anatomical site and imaging the anatomical site with a second imaging modality to generate second imaging data of the anatomical site. A target distortion may be compensated in the stream of ultrasound data with the second imaging data of the anatomical site. The second imaging modality may generate intermittent second modality image data of the target less frequently than the ultrasound camera. For example, the second modality may be a bi-plane x-ray imaging modality.

The step of compensating for distortion in the stream of ultrasound data may include observing a time sequence of positions of the target or a surrogate of the target using the second imaging modality and developing a first motion curve of the target position from the stream of ultrasound image data and a second motion curve of the target position from the second imaging modality data. The step of compensating for distortion in the ultrasound data may further comprise deforming the first motion curve by overlaying the first motion curve with the second motion curve, computing the distortion in the stream of ultrasound image data based on the deformation of the first curve, and subtracting the distortion from the ultrasound image data.

In some embodiments an in-treatment position of the target may be extrapolated based on past observations when an ultrasound camera visibility of the target is below a threshold value. The extrapolation may end when the ultrasound camera visibility of the target is above the threshold value. In some embodiments, the method of compensating for distortion may be used in a radiosurgical treatment of the heart to treat for arrhythmia, for example. Preferably, the method includes estimating ultrasound image quality at a plurality of positions prior to imaging the anatomical site with the ultrasound camera to thereby obtain high quality images of the target In other embodiments of the present invention, a method of increasing accuracy and compensating for distortion in acquired ultrasound image data is provided. The method may include implanting a fiducial marker near a target at an anatomical site and acquiring image data of a position of the fiducial marker with a first imaging modality at discrete intervals. Ultrasound image data of the fiducial marker position may be acquired with an ultrasound camera. A first curve may be fitted to the position data from the first imaging modality and a second curve may be fitted to the position data from the ultrasound camera. The second curve is deformed by overlaying the first curve with the second curve and distortion from the ultrasound image data may be subtracted based on the deformation of the second curve. Preferably, the method includes estimating ultrasound image quality at a plurality of positions prior to imaging the anatomical site with the ultrasound camera.

In some embodiments of the invention, a system for compensating for distortion in acquired ultrasound image data is provided. The system includes an input module configured to receive anatomical site image data from a first imaging modality over discrete intervals, the anatomical site image data comprising a position of a target or a fiducial. The input module may be further configured to receive a stream of anatomical image data from an ultrasound transducer, the ultrasound image data including a position of the target or the fiducial. The system may include a signal processing module coupled with the input module which is configured to fit a first curve to the position of the target or fiducial in the first image modality data and a second curve to the position of the target or fiducial in the ultrasound image data. The signal processing module may deform the second curve by overlaying the second curve with the first curve and remove distortion from the ultrasound image data based on the deformation of the second curve.

Optionally, the system may include an extrapolation module coupled with the input module and the signal processing module. The extrapolation module may be configured to extrapolate an in-treatment position of the target based on past motion when the ultrasound image visibility is low. In some embodiments, the input module may receive anatomical site image data from a second imaging modality. The system may also include an image quality estimation module coupled with the input module which is configured to estimate ultrasound image quality at a plurality of positions. The system may include a display coupled with the image quality estimation module for outputting an indication of the ultrasound image quality at positions relative to the target as estimated by the image quality estimation module.

In other embodiments of the invention, a method for determining a desired position for an ultrasound transducer is provided. The method may include acquiring image data of an anatomical site including a target and estimating an image quality of the ultrasound transducer when imaging the target from a position relative to the imaging target by at least analyzing the acquired image data to estimate ultrasound velocity along a route from the position to the target. The analyzed route may pass through one or more tissue types. The received image data may comprise pre-operative CT image data for example and the route can be evaluated by classifying the route tissue types with their CT intensity values. Image quality of the ultrasound transducer may be estimated by virtually propagating an ultrasound beam along the route and through the one or more tissue types using a ray casting method. Further, image quality of the ultrasound transducer may be estimated by approximating ultrasound transmission at discrete sampling points by calculating a difference between incoming beam strength and tissue absorption and adjusting for reflection.

Preferably, ultrasound image quality at a plurality of positions is estimated to determine a position with the highest imaging quality. Additionally, image quality at a position may be calculated over a time period to determine how the image quality changes with a respiratory and/or a heartbeat motion of the patient. In some embodiments, where the estimated ultrasound velocity along the route from the position to the target can be assumed to not change over the time period, distortion in acquired ultrasound images may be compensated for by a constant gain factor and a constant offset factor. In other situations where the estimated ultrasound velocity along the route from the position to the target varies over the time cycle, distortion in acquired ultrasound images may be compensated for by a dynamic gain factor and a constant offset factor. The dynamic gain factor and offset factor may be calculated from static errors for two or more time steps in the time period of acquired anatomical site image data.

In some embodiments, the image quality estimates may be displayed relative to a three dimensional model of a tissue surface of the anatomical site. Indications may be provided for the estimated imaging quality at each of the positions analyzed. Optionally, the method may include acquiring second image data of the anatomical site including the target at discrete intervals and compensating for a distortion in acquired ultrasound image data using the second imaging data of the anatomical site.

In other embodiments of the invention, a system for estimating ultrasound image quality at a variety of positions to determine a desired ultrasound transducer position is provided. The system includes an input module configured to receive anatomical image data from a first imaging modality and an image quality estimation module coupled with the input module. The image quality estimation module may be configured to estimate ultrasound image quality when imaging the target at a position relative to the target by analyzing the acquired image data to estimate ultrasound velocity along a route from the position to the target. The system may include a display module coupled with the image quality estimation module and configured to output an indication of the ultrasound image quality at positions relative to the target to the user.

The received image data may comprise CT image data and the route may be evaluated by the image quality estimation module by classifying the route tissue types based on their CT intensity values. The image quality estimation module may be configured to virtually propagate an ultrasound beam along the route and through the one or more tissue types using a ray casting method and may estimate ultrasound transmission at discrete sampling points by calculating a difference between incoming beam strength and tissue absorption and adjusting for reflection. The image quality estimation module may be configured to estimate ultrasound image quality over a time period. Further the input module may be configured to receive ultrasound image data and the system may include a signal processing module coupled with the input module. The signal processing module may compensate for distortion in the ultrasound images by a constant or dynamic gain factor and a constant or dynamic offset factor. The signal processing module may use the constant gain factor and the constant offset factor when the estimated ultrasound velocity along the route from the position to the target is assumed to not change over the time period. Alternatively, the signal processing module may use the dynamic gain factor and the dynamic offset factor when the estimated ultrasound velocity along the route from the position to the target varies over the time period. The output of the display module may include a three dimensional model of a surface of the anatomical site with color indications corresponding to estimated ultrasound image quality at positions on the three dimensional model.

Further features of the invention, its nature and various advantages will be more apparent from the accompanying drawings and the following detailed description.

BRIEF DESCRIPTION OF THE DRAWINGS

FIG. 4 illustrates an exemplary method of estimating ultrasound image quality according to embodiments of the invention;

DETAILED DESCRIPTION OF THE INVENTION

The present invention generally provides improved devices, systems, and methods for ultrasound tracking of tissue. The invention is particularly well suited for tracking of moving tissues such as tissues of the heart and tissue structures adjacent the heart that move with the cardiac or heartbeat cycles. The invention may take advantage of radiosurgical structures and methods which have been developed for treating tumors, particularly those which are associated with treatments of tissue structures that move with the respiration cycle. The systems and methods disclosed herein may be used to continuously track movement of a patient's heart during radiosurgical examinations for example. The cardiac cycle is typically considerably faster than the respiration cycle. The overall treatment times can also be quite lengthy for effective radiosurgical procedures on the heart (typically being greater than 10 minutes, often being greater than ½ hour, and in many cases, being two hours or more). Hence, it will often be advantageous to avoid continuous imaging of the target and adjacent tissues using fluoroscopy or the like. A variety of differing embodiments may be employed, with the following description presenting exemplary embodiments that do not necessarily limit the scope of the invention.

Figure 1:
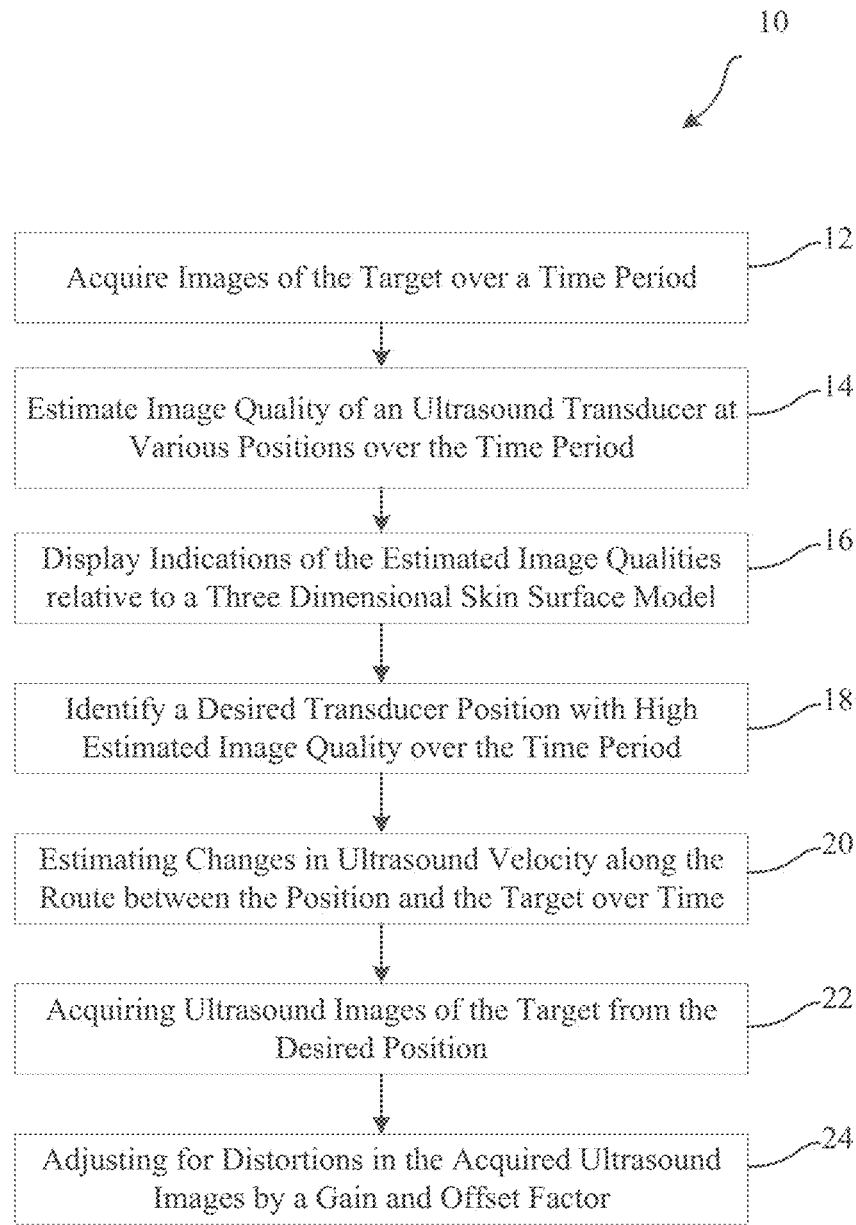
FIG. 1 illustrates an exemplary method of taking ultrasound images according to embodiments of the invention.

FIG. 1 illustrates an exemplary method 10 of estimating ultrasound image quality at ultrasound positions relative to a target. At step 12, pre-treatment images of the target are acquired, typically over a time period. At step 14, the pre-treatment images may be used to estimate image quality of an ultrasound transducer at various positions relative to a target. The image quality may be estimated over the time period. At step 16, the image quality estimates for one or more positions may be displayed to an operator, preferably relative to a three-dimensional surface model of the patient. At step 18, a desired transducer position may be identified which has a high estimated image quality. The desired transducer position may have the highest averaged image quality over a given time period. At step 20, ultrasound velocity along the route from the desired transducer position to the target may be analyzed to determine whether the ultrasound velocity along the route stays relatively constant or whether it varies with time. At step 22, ultrasound images of the target may be acquired from the desired position. At step 24, distortion in the ultrasound images may be compensated for using a gain and offset factor calculated from the information obtained in step 20. Advantageously, an ultrasound operator may be able to quickly identify and visualize the optimal positions for an ultrasound transducer prior to imaging a target by utilizing the disclosed method. Further, the ultrasound operator may be able to visualize how the image quality may change from a plurality of positions with patient movement from a respiratory motion and/or a heartbeat motion. Moreover, distortions in the acquired ultrasound images may be compensated by using the methods disclosed herein.

The pre-treatment image data acquired 12 include the anatomical site and the target tissue. The image data may be a two dimensional single CT scan or a three dimensional CT scan. Further the pre-treatment image data may be acquired over a time period in order to capture anatomical site and target movement during a heartbeat cycle and/or a respiratory cycle motion of the patient. These scans may also be used for the contouring of the target region and the calculation of the dose distribution during radiosurgical treatment planning. The scans may come from other imaging modalities such as MRI, PET, etc.

Figure 2:
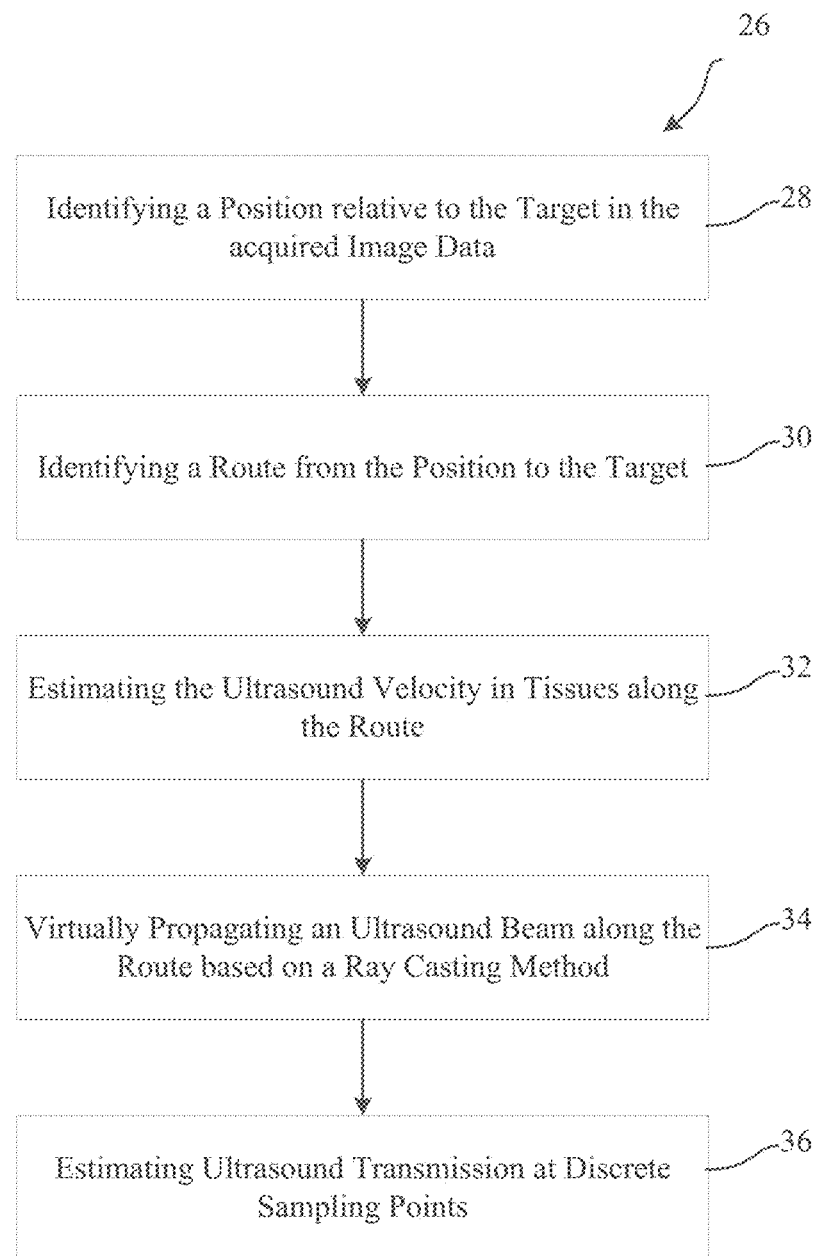
FIG. 2 illustrates an exemplary method of estimating ultrasound image quality according to embodiments of the invention.

FIG. 2 illustrates an exemplary method 26 of estimating the image quality of a transducer placed at a certain skin position 14. The method starts at step 28 by identifying an ultrasound transducer position relative to the target in the acquired image data. At step 30, a route from the transducer position to a chosen target position inside the volume is analyzed. At step 32, the ultrasound velocity in tissues along the route is estimated. At step 34, an ultrasound beam may be virtually propagated from the position and along the route based on a ray casting method. At step 36, ultrasound transmission may be estimated at discrete sampling points to estimate overall ultrasound image quality.

Figure 3:
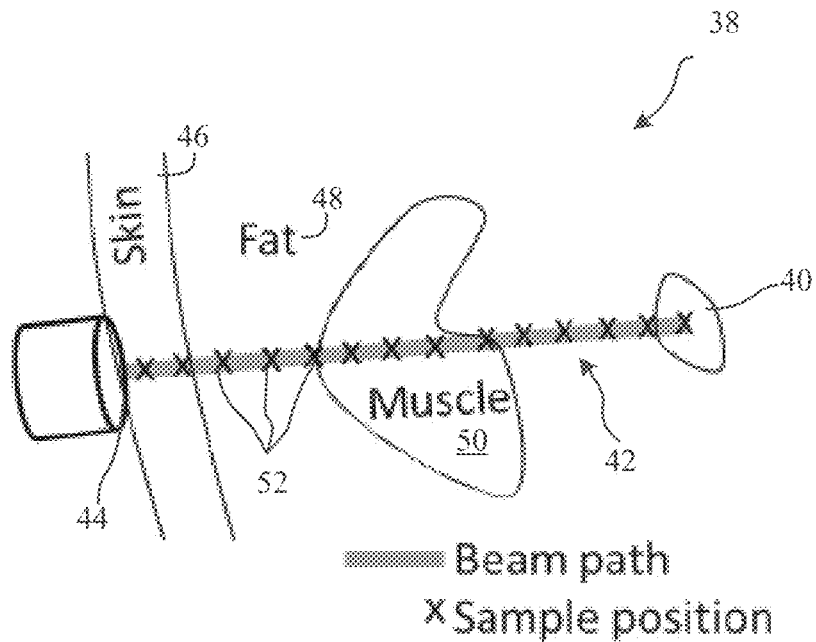
FIG. 3 provides an exemplary table mapping Hounsfield values to acoustic properties.

To estimate the imaging quality of a transducer placed at a certain position, the route from the transducer position to a chosen target position inside the volume must be analyzed. For a good view of the target one consideration is the absorption of the ultrasound beam travelling forth and back between the target and the transducer. The estimation of beam strength can be calculated based on beam transmission and reflection as the main parts in beam absorption. FIG. 3 illustrates an exemplary pre-treatment scan 38 of the anatomical site including the target 40. A route 42 from a transducer position 44 to the target 40 is determined. The tissues which the route 42 passes through can be determined from the pre-treatment image data. Tissue types may be classified by using the acquired pre-treatment image data. For example, where the pre-treatment data is one or more CT scans, the tissue types may be classified with respect to their CT intensity values. FIG. 4 provides an overview of tissue in the region of the heart and their corresponding Hounsfield units. The exemplary route 42 illustrated in FIG. 3, passes through skin 46, fat 48, and muscle 50 in order to arrive at target 40 from the transducer position 44. Afterwards, the ultrasound beam is virtually propagated through the CT volume using a ray casting method. For every discrete sampling point 52, the ultrasound transmission is calculated as a difference of incoming beam strength and tissue absorption. The reflection may be calculated by:

$$R = (Z_2 - Z_1)^2 / (Z_2 + Z_1)^2 \qquad (1)$$

Where $Z_1$ and $Z_2$ represent the acoustic impedances at the current and previous sampling point, is additionally subtracted. Given all possible transducer positions 44 on the patient's chest, a desired ultrasound transducer position maximizes the ultrasound transmission between transducer and target. In some embodiments, the target visibility over time may be calculated where the desired position is computed as the weighted maximum visibility over all time steps of a 4DCT. Additionally, embodiments may take advantage of enhanced beam strength computation by adjusting for interference, refraction, diffraction and beam diffusion. Further, methods may include additional visibility analysis by analyzing target reflection, entropy in target region, and complete ultrasound image simulation. The methods may take a simulated ultrasound image and detect, at which quality the target is visualized inside. The easiest way to do it may be to accumulate the brightness in this area. An enhanced method may be to measure the entropy or the amount of edges/intensity gradients inside the image. All gradients could be summed to one value indicating the image quality.

Figure 5A:
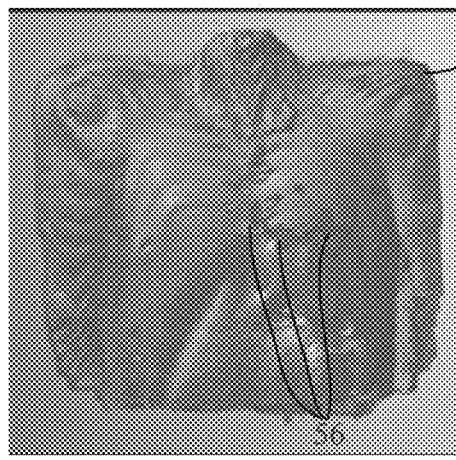
FIGS. 5A-5B illustrate a display of the output of ultrasound image quality estimates calculated according to methods of the present invention relative to preferred ultrasound transducer positions identified by an ultrasound technician.
Figure 5B:
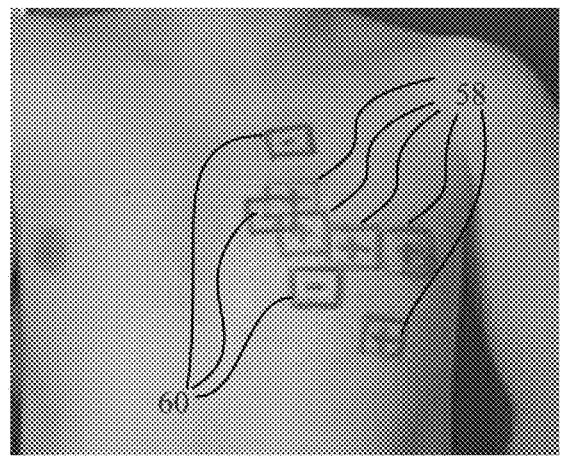

After image quality estimation 14, the results may be displayed to an operator 16. Preferably, a plurality of image quality estimations 14 are calculated according to the methods disclosed herein. Indications of the image quality at each position may inform an operator which positions are best for imaging a target using an ultrasound transducer. In a preferred embodiment, the indications of image quality are displayed relative to a three dimensional model of the patient. The image quality indications may comprise a color coding on the three dimensional model. For example, FIG. 5A displays the computed image quality of transducer positions according to methods of the present invention. As shown in FIG. 5A, a three-dimensional model 54 of the patient can be constructed from the pre-treatment image data. The blue indications 56 on the three-dimensional model indicate positions which have high estimated image quality. FIG. 5B shows the ultrasound windows as determined by a radiologist. The positive windows 58 illustrate the preferred windows for measuring the target tissue while the negative windows 60 illustrate undesired windows. As can be appreciated from FIGS. 5A and 5B, the methods of estimating ultrasound image quality prior to imaging disclosed herein correspond to the positive windows 58 which were determined by the radiologist. It may be worth noting that positive window 62 which was added by the radiologist required a lot of pressure to obtain a reasonable image and accordingly, the ultrasound image quality estimation did not include a corresponding positive window.

Figure 6:
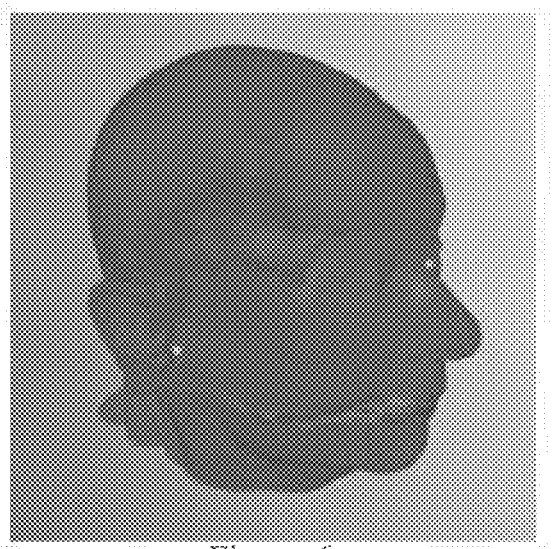
FIG. 6 illustrates a display of the output of ultrasound image quality estimates calculated according to methods of the present invention for imaging the substantia nigra.
Figure 7A:
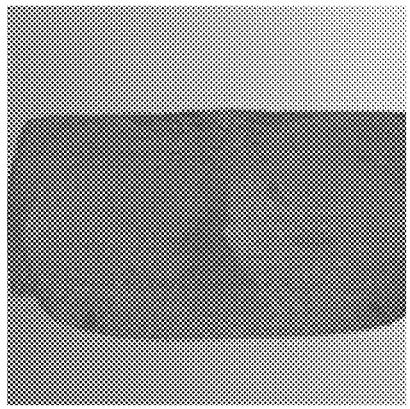
FIGS. 7A-7E illustrate optimal windows for visualizing the RUPV for different patients according to methods of the present invention.
Figure 7B:
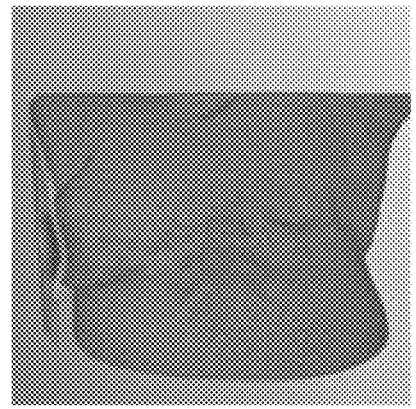
Figure 7C:
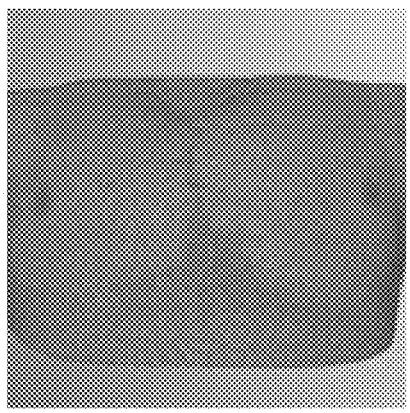
Figure 7D:
Figure 7E:
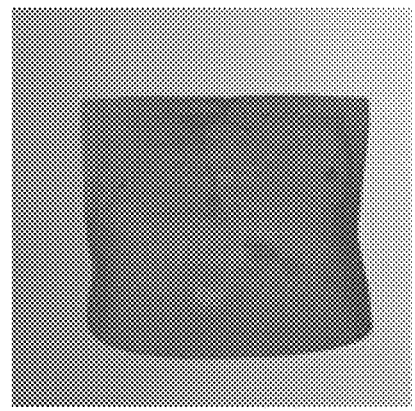

FIG. 6 illustrates another exemplary display of image quality estimates as determined by methods disclosed herein. The high quality windows for imaging the substantia nigra is displayed. This type of imaging may provide for the early detection of Parkinson's disease. FIGS. 7A-7E illustrate the optimal viewing windows for visualizing the RUPV for different patients as computed by the methods disclosed herein.

Figure 8:
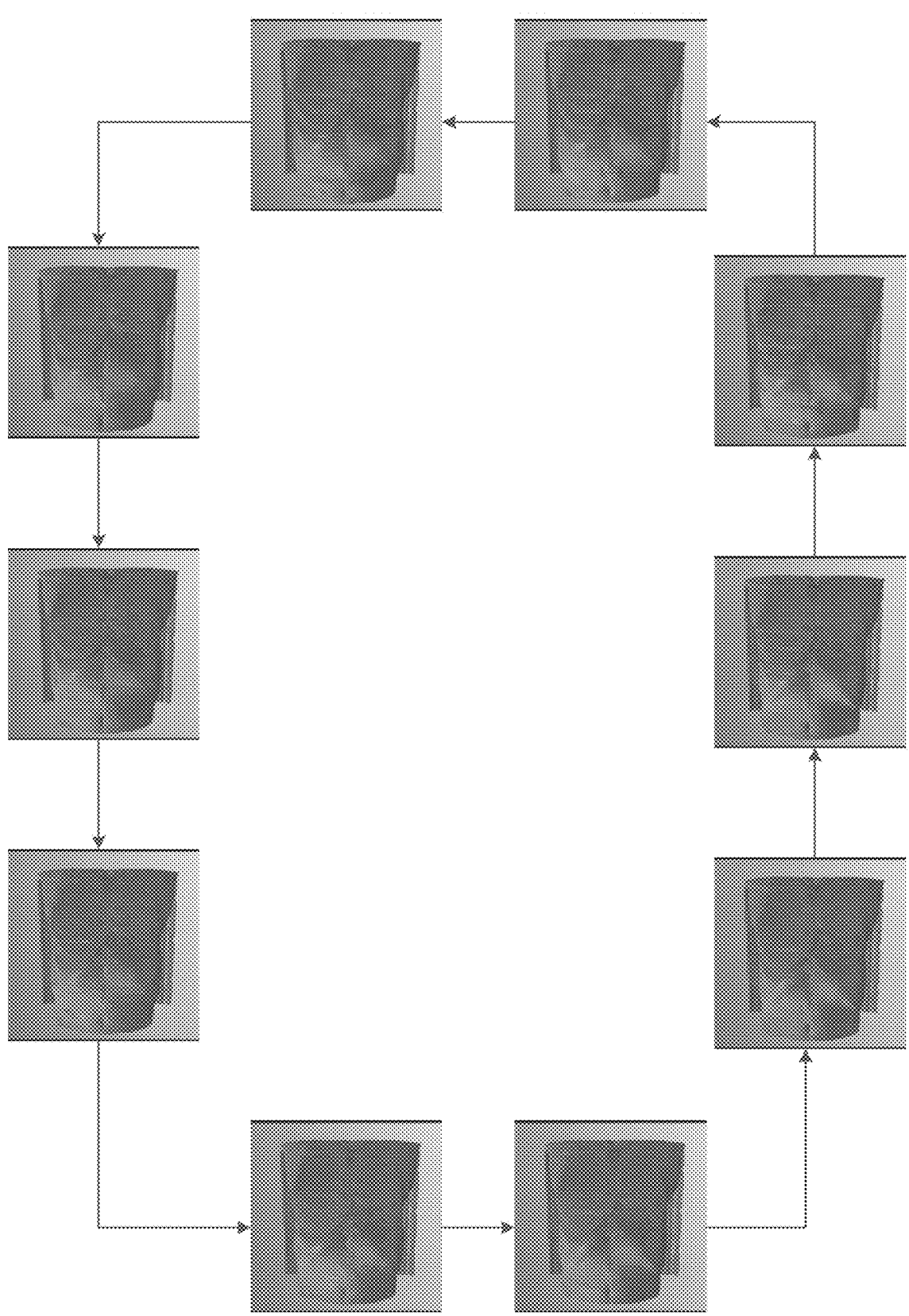
FIG. 8 illustrates optimal windows for visualizing the septum for eight time steps according to methods of the present invention.

As discussed above, image quality estimation may be performed for a plurality of time steps to indicate how image quality may change with a patient respiratory and/or heart beat motion. FIG. 8 illustrates the optimal windows for visualizing the septum over eight time steps. The optimal windows may vary slightly over the eight time steps. Image quality may also be estimated at varying frequencies as needed. For example, the quality may be estimated at higher frequencies for target tissues which have fast tissue movements such as the heart. Image quality may be estimated at lower frequencies for tissues which relatively slower motions. Accordingly, the operator may choose a transducer position with the highest average image quality over the time period for visualizing a target tissue.

After estimating the ultrasound image quality at one or more positions 14, steps may be taken to minimalize distortion or to compensate for distortion in any acquired ultrasound images. The distance in ultrasound scans may be computed as:

$$\text{Distance} = \text{Time} * \text{Velocity} \quad (2)$$

This ultrasound velocity cannot be measured by the ultrasound transducer and is commonly approximated by 1540 m/s as a mean speed of sound for the penetrated tissue. While this may be a good approximation for visualization, it theoretically allows for errors of up to five percent in the distance calculation. In a worst-case scenario, a target at a distance of 150 mm may be distorted in forth/back direction by up to 7.5 mmm including an uncertainty of 15 mm. While the theoretical error is relatively unlikely, distortions of up to two percent (e.g., 3 mm at 150 mm distance) are commonly present.

In some embodiments, distortions can be derived from the pre-treatment image data, such as a CT volume, and used for compensation. Preferably, an optimization of the transducer position may be used as an a priori strategy to minimize the expected velocity changes and the necessity to dynamically correct for them.

As seen above, tissue ultrasound properties can be estimated based on acquired pre-treatment data. For example, when pre-treatment data comprises CT image data, ultrasound properties can be sufficiently mapped to CT Hounsfield units for a particular anatomical region. An ultrasound transducer may be virtually placed at the skin surface and the acoustic properties including velocity differences can be computed from CT data. Assuming constant velocity errors between transducer and target, a simple function using the two compensation factors, Gain and Offset can be applied to correct for distortions:

$$\text{Corrected distance} = f(\text{Distance}, \text{Gain}, \text{Offset}) \quad (3)$$

The distortion of the relative target movement may be low and may be neglected. The gain and offset may be calculated with the provided set of two corresponding positions/distances in ultrasound and a secondary modality. Then a function may be used to linearly undistort the ultrasound volume:

$$\text{real\_distance} = f(\text{ultrasound\_distance}) = \text{offset} + \text{gain} * \text{ultrasound\_distance}. \quad (4)$$

Figure 9:
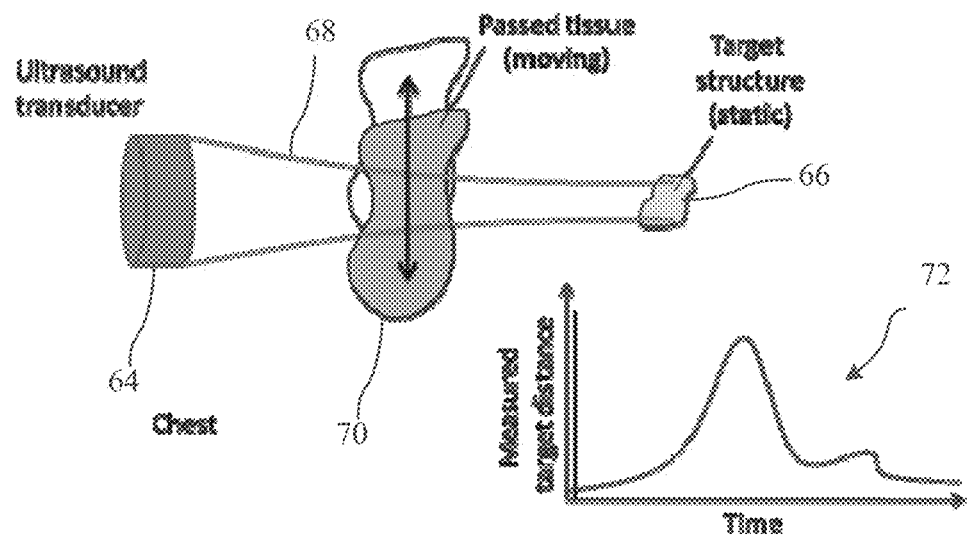
FIG. 9 illustrates a situation where estimated ultrasound velocity along a route from the ultrasound transducer position to the target may vary over time.

In situations with time-varying errors due to non-uniform movements in the beam path, the absolute and even the relative target movements can be compensated. FIG. 9 illustrates a situation where a movement along the beam path induces a non-existing target movement in the distance measurements. Ultrasound transducer 64 may be imaging target 66 from a route 68. Route 68 passes through a tissue 70 which moves during a patient's respiration and/or heartbeat motion. Accordingly, even though target 66 is static, the measured target distance 72 may vary over time due to the motion of tissue 70.

The quality of the compensation depends on the available data. In the case of only one CT volume, static distortions may be compensated for quite well. Error sources may include errors from mapping ultrasound properties according to CT Hounsfield units and ultrasound model complexity. Compensation for static error can include a measurement of static errors using the CT image data and a static offset and gain compensation. Resulting image quality may be very good. In situations where the target is moving, it is preferable to have a series of pre-treatment scans available to compensate for errors. It may be difficult to calculate for distortion since target motion is unknown with only a single CT volume. In situations where only a single CT volume is available, a statistical approach may be used to compensate for distortion. Alternatively, the assumption of the common mean ultrasound velocity may be used. When 4DCT data is available, error sources may include errors from mapping ultrasound properties according to CT Hounsfield units and ultrasound model complexity. A further error source may be introduced in the identification of the current time step. Error may be compensated by a measurement of static errors over all time steps. Thereafter, a dynamic gain and offset compensation may be calculated to reduce distortions due to respiratory and/or cardiac motion. Accordingly, ultrasound image data distortion may be compensated when the target is static or when the target is in motion by using the acquired pre-treatment data.

Another method of minimizing distortion in ultrasound transducer image data comprises minimizing the distance between the ultrasound transducer and the target. The distance may be simply added as a factor into the quality function of the search algorithm given above.

$$\text{Position quality} = a*\text{Transmission} + b*\text{Distance} \quad (5)$$

When 4DCT data is available, minimizing distortion may include measuring the absolute distortion or the distortion change (combined with static distortion correction) over time for every possible transducer position and minimize them in order to find an optimal transducer position.

$$\text{Position quality} = a*\text{transmission} + b*\text{Distortion Change} \quad (6)$$

Figure 10:
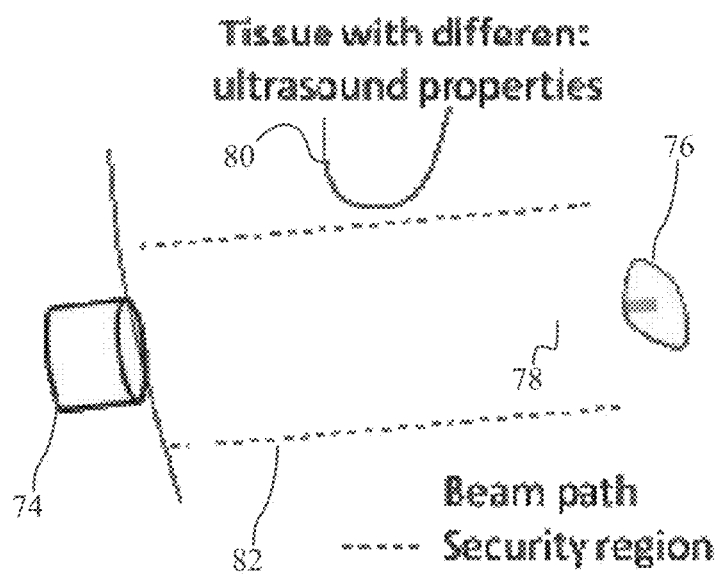
FIG. 10 illustrates a situation where estimated ultrasound velocity along a route from the ultrasound transducer position to the target stays relatively constant over time.

When CT image data of a single time step is available, transducer positions where tissue velocities are similar for a cylindrical volume around the beam path may be preferred. FIG. 10 illustrates such an example. In this situation, transducer 74 may be imaging target 76 along route 78. A tissue 80 with a different ultrasound property may have a motion associated with patient respiratory or heartbeat motion, however the tissue 80 and its motion may be disposed outside of a security region 82. Accordingly, the transducer position may be selected to make it less likely that tissue with different velocity properties enters the beam path and induces time-varying distortions. Thus the methods disclosed herein may be used to select ultrasound transducer positions which limit the amount of distortion in image data by limiting the chances of a time-varying ultrasound velocity along the ultrasound transducer route.

As discussed above, the methods disclosed above may be used to track target tissues during radiosurgical treatments and systems such as those disclosed in related U.S. patent application Ser. No. 11/971,399 entitled Depositing Radiation in Heart Muscle under Ultrasound Guidance, the entire disclosure of which is incorporated herein by reference. A stereotaxic radiation treatment device typically includes a beaming device, which is also called the beam source. This beam source produces a beam of radiation. The beam source can be moved to different locations. In this way, the beam can be directed towards the target. Targets are typically tumors, but other lesions can also be treated with this method. In commercially available systems for radiosurgery, the beam source is mounted to a robotic arm. This arm is freely programmable, and can move the beam source to appropriate locations in space. It can also move the beam source in such a way that the beam tracks the motion of a moving target. The motion of the target occurs when the tumor is close to the heart or the lung, and is due to the heartbeat or the respiratory motion of the patient's chest. Prior to treatment, a CT or an MR may be taken from the anatomical site/region of interest. The target is then marked in the resulting stack of images or may be marked relative to a three-dimensional image model of the target region according to the methods and systems disclosed in related application Ser. No. 12/838,308 entitled Heart Tissue Surface Contour-Based Radiosurgical Treatment Planning, the entire disclosure of which is incorporated herein by reference.

Radiosurgical systems typically track target tissue using a bi-planar x-ray system, however there are advantages of reducing the amount of patient exposure to radiation. While ultrasound tracking of target tissues has been proposed, distortion in ultrasound image data may make such tracking insufficient since target tracking during radiosurgical treatments must be very accurate, especially for target tissues, such as heart tissues, which move relatively rapidly with patient respiration motion and/or heartbeat motion.

Figure 11:
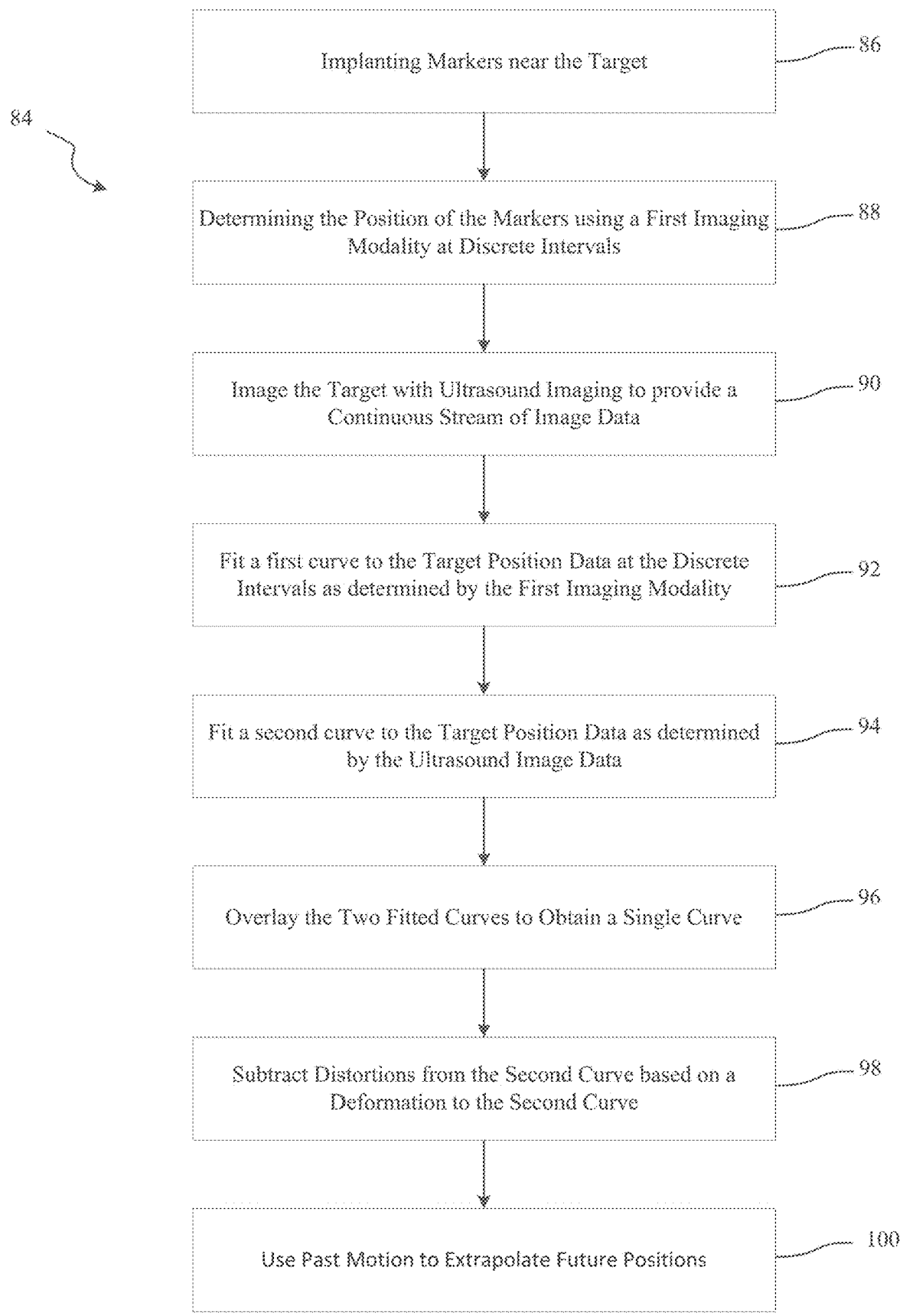
FIG. 11 illustrates an exemplary method of compensating for distortion in ultrasound image data.

FIG. 11 illustrates another method 84 of reducing distortions in acquired ultrasound imaging data and/or for tracking target tissues during a radiosurgical procedure. At step 86, markers may be implanted at or adjacent to the target tissue if the target tissue cannot be easily distinguished in imaging data. At step 88, the position of the target tissue is determined using a first imaging modality to image the target tissue and/or the implanted markers at discrete intervals. At step 90, the position of the target tissue is determined using an ultrasound imaging device to image the target tissue and/or the implanted markers to provide a continuous stream of imaging data. At step 92, a first curve is fitted to the target tissue position data at the discrete intervals as determined by the first imaging modality. At step 94, a second curve is fitted to the target tissue position data as determined by the ultrasound imaging device. At step 96, the first curve and the second curve are overlaid to obtain a single curve. At step 98, distortion in the ultrasound image data may be subtracted based on the deformation of the ultrasound curve from the overlaying of the two curves. At step 100, current positions of the target tissue may be extrapolated based on past motion during times of poor ultrasound imaging.

In some methods of the present invention, markers may be implanted near a target 86. These markers may be, for example, gold markers which are implanted in or near a target tissue. The markers may be used to better identify a target tissue in subsequently captured images. The exact position of the target tissue and/or implanted markers may be determined by a first imaging modality 88. The first imaging modality may be a stereo x-ray imaging system which typically accompanies radiosurgical systems. Continuous imaging is discouraged due to radiation exposure of the patient and technical limitations of the x-ray imaging systems available commercially. The acquisition of images with the stereo x-ray imaging system may be repeated several times before treatment. This gives a series of exact positions of the target obtained with x-ray imaging. However, this series may not be continuous and may not present real-time information on the target location. Accordingly, the ultrasound camera may be used to yield a continuous stream of images 90, where each image has the target located. As discussed above, the target location may be identified with high speed automatically by using a template matching algorithm. This stream may contain more than 20 images per second.

A first curve may be fitted to the position data obtained by the stereo x-ray imaging system 92 and a second curve may be fitted to the position data acquired by the ultrasound image data 94. Since the second curve is obtained with ultrasound, it will be subject to distortion. The first such curve is free of distortion. After fitting the first and second curves to the acquired position data, the two curves are overlaid to obtain a single undistorted curve 96 with points sufficiently densely spaced along the curve such that real-time tracking of the target is possible.

Figure 12:
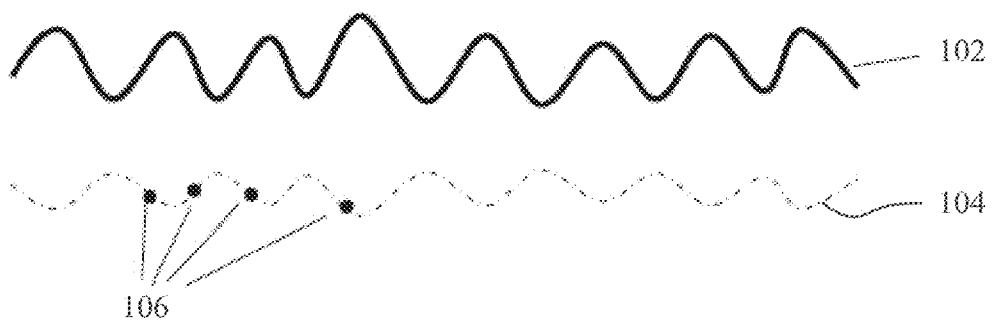
FIG. 12 illustrates a first motion curve fitted to ultrasound data relative to a second motion curve fitted to intermittently acquired image data from another imaging modality.

FIG. 12 illustrates the two curves representing position information for the target. For example, each curve can represent the motion of the target along the x-axis of the base coordinate system used for the treatment. The curve 102 shows the distorted curve of target positions obtained from analyzing the ultrasound images. The curve 104 may not be fully known during treatment, and only a small number of positions 106 along this curve are known. Since both curves must show the same motion, they can be aligned. After alignment, the ultrasound curve 102 is deformed in such a way that the points 106 will closely match the curve 104. The deformation thus obtained is then expressed as a function and can be used to obtain undistorted position information 98 for the new ultrasound images received after switching of the x-ray imaging device. An ultrasound image may be acquired along the beam path from transducer to target and back. Distortions may be mostly caused by differences of the speed of sound in different tissue. This may be a non-linear distortion along the beam path and (to have the best fitting) a non-linear function:

$$f(\text{ultrasound\_distance}) = \text{real\_distance} \quad (7)$$

has to be found for undistortion. This may be a table, which can be approximated by a polynomial function.

An ultrasound imaging camera must be placed in a position with good visibility on the patient's skin surface. In a preferred embodiment of the present invention, the method includes obtaining an optimal placement of the ultrasound camera 10. As discussed above, a simulation of the physical properties of the ultrasound imaging device is used. This simulation may rely on the CT or MR data obtained before treatment.

Figure 13:
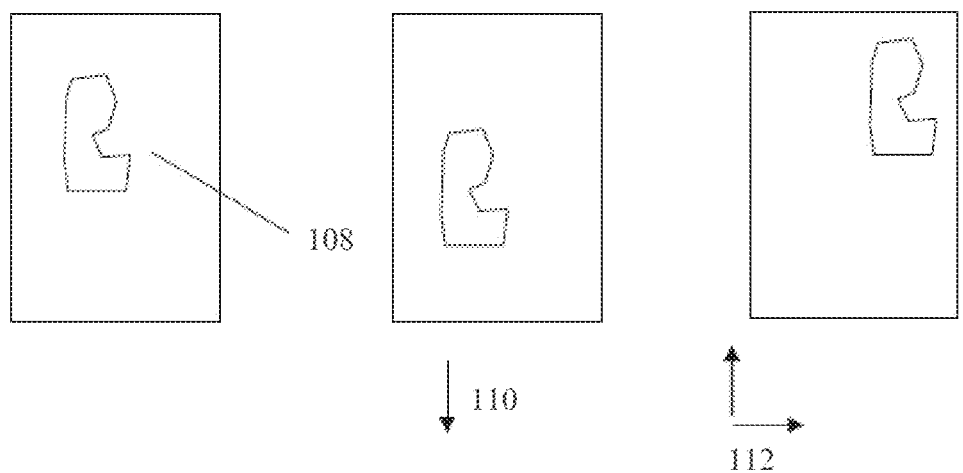
FIG. 13 illustrates an exemplary method of extrapolating target position based on past tissue motion.

In another preferred embodiment in accordance with the present invention, the past curve of the motion obtained with the ultrasound system is used to extrapolate current and future positions 100. This may be done to overcome periods of poor visibility in the ultrasound image. FIG. 13 shows several positions of a target as seen in an ultrasound image. In each image, the target occurs shifted, either in vertical or horizontal direction. A template may be delineated by the user in the first image 108. Cross correlation is used to compute the shifting offsets 110 and 112 for obtaining the new position of the target.

In a further embodiment of the invention, the x-ray imaging system is used to locate small markers attached to the ultrasound camera. In this way, the relative positions of the ultrasound camera can be computed in the same coordinate system as that of the treatment device.

Figure 14:
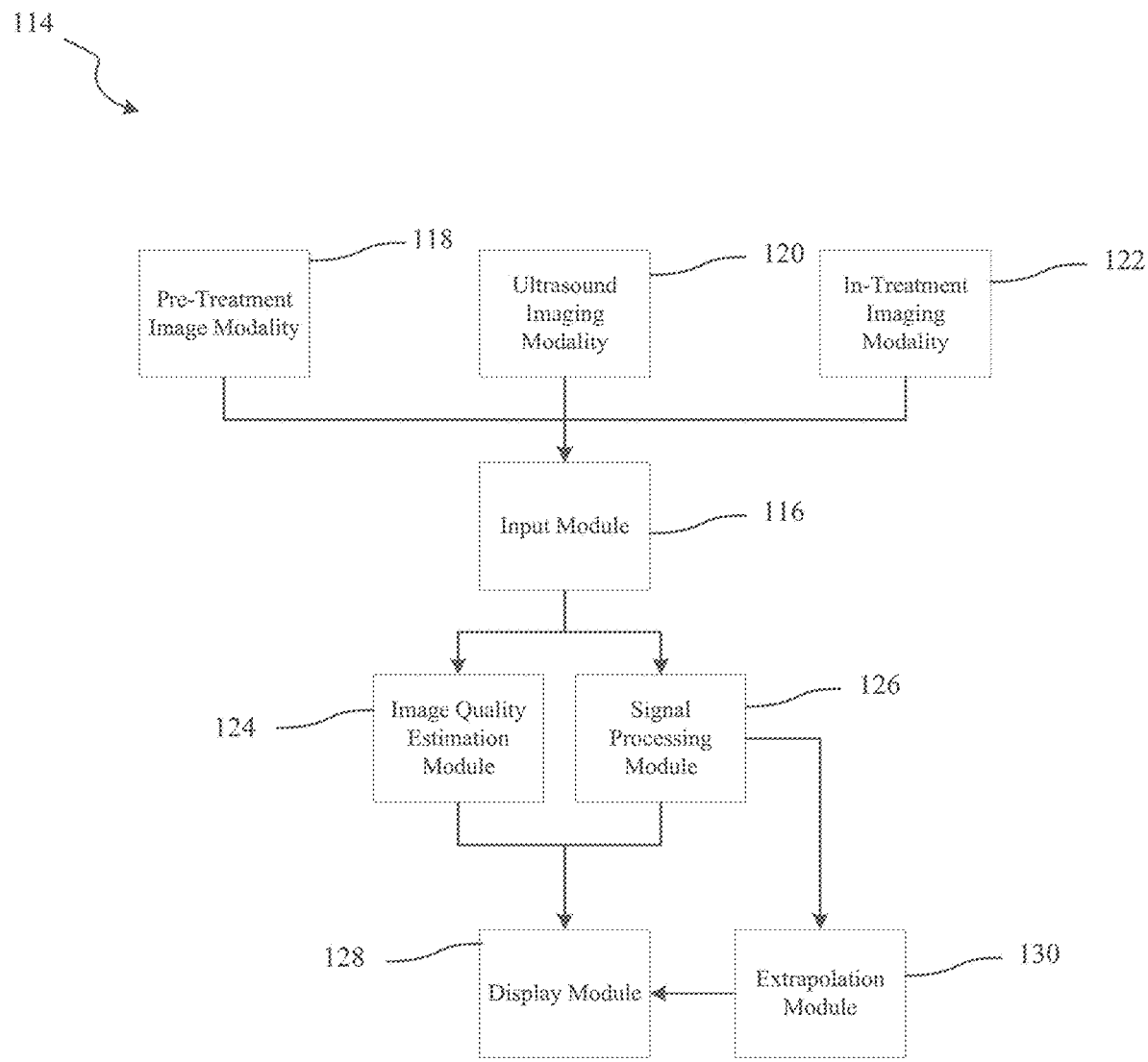
FIG. 14 illustrates a system for estimating ultrasound image quality at various positions and/or compensating for distortions in ultrasound image data.

FIG. 14 illustrates a system 114 for compensating for distortions in ultrasound images. The system 114 may include an input module 116 for receiving: 1) pre-treatment images of an anatomical site including the target from a pre-treatment imaging modality 118; 2) ultrasound images of the anatomical site including the target from an ultrasound imaging modality 120; and 3) in-treatment images of the anatomical site including the target from an in-treatment imaging modality 122. An image quality estimation module 124 may be coupled with the input module 116 for estimating ultrasound image quality at various positions relative to the target. A signal processing module 126 may be coupled to the input module 116 for adjusting for distortions in acquired ultrasound image data by using acquired pre-treatment image data or in-treatment image data. The output from the image quality estimation module 124 and the signal processing module 126 may be displayed to an operator by using a coupled display module 128. In a preferred embodiment, system 114 includes an extrapolation module 130 for calculated current or future target position based on past target motion.

The image quality estimation module 124 may use acquired pretreatment images of the anatomical site to estimate ultrasound image quality at a plurality of positions to determine a desired ultrasound transducer. The image quality estimation 124 module may estimate image quality over a time period, such as a time period over a patient respiratory motion and/or heartbeat motion. The signal processing module 126 may be configured to compensate for distortions in acquired ultrasound image data by using methods disclosed herein and acquired pre-treatment images of the target area or acquired in-treatment image data, such as stereo x-ray images. The display module 128 may be configured to output the ultrasound image quality estimates relative to a three dimensional model of the patient.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

The embodiments discussed herein are illustrative. As these embodiments are described with reference to illustrations, various modifications or adaptations of the methods and/or specific structures described may become apparent to those skilled in the art after reading the above disclosure.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An ultrasound tissue imaging method comprising:
imaging a target with an ultrasound transducer to generate a stream of ultrasound data of the target, wherein the target is included within or adjacent to an anatomical site;
imaging the anatomical site with a second imaging modality to generate second imaging modality data of the anatomical site;
compensating for a distortion in the stream of ultrasound data using the second imaging modality data of the anatomical site so as to generate compensated data; and
transmitting the compensated data;

wherein the step of compensating for a distortion in the stream of ultrasound data further comprises:
   observing a time sequence of positions of the target or a surrogate of the target using the second imaging modality;
   developing a first motion curve of the positions of the target or a surrogate of the target from the stream of ultrasound image data and a second motion curve of the positions of the target or a surrogate of the target from the second imaging modality data;
   deforming the first motion curve by overlaying the first motion curve with the second motion curve;
   computing the distortion in the stream of ultrasound data based on the deformation of the first curve; and
   subtracting the distortion from the ultrasound image data.

2. The method of claim 1, wherein the second imaging modality generates the second imaging modality data of the anatomical site at a lower rate than the ultrasound transducer generates the stream of ultrasound data; and wherein the second imaging modality comprises a biplane x-ray imaging modality.

3. The method of claim 1, further comprising extrapolating an in-treatment position of the target based on past observations of the stream of ultrasound data; wherein extrapolating the in-treatment position of the target occurs when an ultrasound transducer visibility of the target is below a threshold value; and wherein extrapolating the in-treatment position of the target ends when the ultrasound transducer visibility of the target is above the threshold value.

4. The method of claim 1, further comprising estimating ultrasound image quality at a plurality of positions prior to imaging the anatomical site with the ultrasound transducer.

5. The method of claim 4, wherein the step of estimating image quality of the ultrasound transducer further comprises virtually propagating an ultrasound beam along a route from the ultrasound transducer to the target through one or more tissue types using a ray casting method.

6. The method of claim 1, further comprising:
   calculating an estimated characteristic of ultrasound imaging of the target with the ultrasound transducer from a plurality of candidate positions relative to the target using the stream of ultrasound data, the second imaging modality data, or both the stream of ultrasound data and the second imaging modality data by estimating ultrasound velocity along one or more routes from each of the plurality of candidate positions to the target, the one or more routes passing through one or more tissue types; and
   selecting a desired position from among the plurality of candidate positions for the ultrasound transducer using the estimated characteristic of ultrasound imaging calculated for each of the plurality of candidate positions.

7. The method of claim 6, wherein the anatomical site and target are imaged by a CT system to provide the second imaging modality data; and wherein the one or more routes are evaluated by at least classifying the one or more tissue types through which the one or more routes passes with their CT intensity values.

8. The method of claim 6, further comprising estimating an image quality of the ultrasound transducer when imaging the target from one or more of the plurality of candidate positions other than the desired position relative to the target and determining which of the one or more of the plurality of candidate other positions other than the desired position has the highest imaging quality.

9. The method of claim 8, wherein the step of estimating image quality of the ultrasound transducer further comprises virtually propagating an ultrasound beam along the one or more routes and through the one or more tissue types using a ray casting method.

10. The method of claim 8, wherein the step of estimating image quality of the ultrasound transducer further comprises estimating ultrasound transmission at discrete sampling points by calculating a difference between incoming beam strength and tissue absorption and adjusting for reflection.

11. The method of claim 6, wherein the second imaging modality data is acquired over a time period and the time period includes a heartbeat cycle, a respiratory cycle, or both the heartbeat cycle and the respiratory cycle; wherein an image quality of the ultrasound transducer at the desired position is estimated over the time period.

12. The method of claim 11, wherein the estimated ultrasound velocity along the one or more routes from the desired position to the target is assumed to not change over the time period, and wherein the step of imaging a target with the ultrasound transducer occurs with the ultrasound transducer at the desired position, and wherein the step of compensating for the distortion in the stream of ultrasound data further comprises using a constant gain factor and a constant offset factor.

13. The method of claim 11, wherein the estimated ultrasound velocity along the one or more routes from the desired position to the target varies over the time cycle, and wherein the step of imaging a target with the ultrasound transducer occurs with the ultrasound transducer at the desired position, and wherein the step of compensating for the distortion in the stream of ultrasound data further comprises using a dynamic gain factor and a dynamic offset factor; wherein the dynamic gain factor and the dynamic offset factor are calculated from static errors for two or more time steps in the time period of generating second imaging modality data of the anatomical site.

14. The method of claim 6, further comprising:
   estimating an image quality of the ultrasound transducer when imaging the target from one or more of the plurality of candidate positions other than the desired position relative to the target;
   displaying a three dimensional model of a tissue surface of the anatomical site;
   displaying an indication on the three dimensional model at one or more of the positions, wherein the indication corresponds to the estimated image quality at the position;
   acquiring additional ultrasound image data of the anatomical site; and
   compensating for an additional distortion in the additional ultrasound image data using the second imaging data of the anatomical site.

* * * * *